United States Patent [19]
Owen

[11] Patent Number: 5,456,714
[45] Date of Patent: Oct. 10, 1995

[54] TUBULAR SURGICAL IMPLANT HAVING A LOCKING RING AND FLANGE

[76] Inventor: Earl R. Owen, Microsurgery Centre, 1 Esther Street, Surry Hills, NSW 2010, Australia

[21] Appl. No.: 170,312
[22] PCT Filed: Jul. 3, 1992
[86] PCT No.: PCT/AU92/00328
§ 371 Date: Jan. 3, 1994
§ 102(e) Date: Jan. 3, 1994
[87] PCT Pub. No.: WO93/00868
PCT Pub. Date: Jan. 21, 1993

[30]     Foreign Application Priority Data

Jul. 4, 1991 [AU] Australia .................. PK7057

[51] Int. Cl.⁶ ............................................... A61F 2/06
[52] U.S. Cl. .................. 623/1; 623/12; 604/8; 606/151; 606/153
[58] Field of Search .............. 623/1, 12; 604/8; 606/151, 153

[56]             References Cited

U.S. PATENT DOCUMENTS

| | | | |
|---|---|---|---|
| 2,638,901 | 5/1953 | Sugarbaker | 606/153 |
| 3,540,451 | 11/1970 | Zeman | 604/8 |
| 3,713,441 | 1/1973 | Thomas | 604/8 |
| 4,233,981 | 11/1980 | Schomacher | 128/334 |
| 4,368,736 | 1/1983 | Kaster | 128/334 |
| 4,523,592 | 6/1985 | Daniel | 606/153 |
| 5,250,058 | 10/1993 | Miller et al. | 606/153 |

FOREIGN PATENT DOCUMENTS

| | | |
|---|---|---|
| 0269254 | 6/1988 | European Pat. Off. . |
| 2657255 | 6/1978 | Germany . |
| 1593651 | 9/1990 | Russian Federation . |
| 8201644 | 5/1982 | WIPO . |
| 8806865 | 9/1988 | WIPO . |
| 9015582 | 12/1990 | WIPO . |

*Primary Examiner*—Paul B. Prebilic
*Attorney, Agent, or Firm*—Ostrolenk, Faber, Gerb & Soffen

[57]             ABSTRACT

A tubular surgical implant for joining to a wall of a vessel or hollow organ is disclosed such that the implant opens into the interior of the vessel or organ. The implant has an open ended tube, a deformable flange at one end of the tube, a plurality of spikes extending from the flange, alongside and generally parallel to the tube, and a locking ring arranged to slide axially on the tube, the locking ring incorporating a plurality of holes aligned with and adapted to received the spikes.

10 Claims, 3 Drawing Sheets

TUBULAR SURGICAL IMPLANT HAVING A LOCKING RING AND FLANGE

TECHNICAL FIELD

This invention relates to a tubular surgical implant and has been devised particularly though not solely for use as a by-pass device and specifically as a coronary by-pass device.

BACKGROUND ART

So-called "heart by-pass" surgery is relatively common and is necessitated by blockage or partial blockage and narrowing of the coronary arteries causing ischaemia or a lack of blood supply to the heart muscle, distally. The pain felt as a result is known as angina and the result can be heart attack, death or recovery with damage to the heart muscle. The present treatment by way of heart by-pass surgery is effective but is expensive to carry out, time consuming, and requires stopping the heart and placing the patient on a life-support artificial heart lung machine using large quantities of blood. Surgeons must then harvest leg veins or cheer arteries or both to sew into position as a by-pass from the aorta to the distal coronary artery.

It is desirable to provide a much less complicated procedure for carrying out a by-pass operation, which is not only faster and lean expensive to perform, but also results in less risk to the patient.

DISCLOSURE OF THE INVENTION

The present invention therefore provides a tubular surgical implant adapted to be joined to a wall of a vessel or hollow organ such that the implant opens into the interior of the vessel or organ, said implant comprising an open ended tube, a deformable flange at one end of the tube, a plurality of spikes extending from the flange, alongside and generally parallel to the tube, and a locking ring arranged to slide axially on the tube, the locking ring incorporating a plurality of holes aligned with and adapted to receive the spikes.

Preferably the locking ring is keyed to the tube, preventing rotation of the ring relative to the tube, Preferably the spokes and the holes in the locking ring are provided with a locking mechanism arranged to retain the spikes within the holes when the locking ring is engaged with the spikes.

The flange may be deformable relative to the tube such that the flange may be deformed to lie against the tube for insertion into an opening in the wall of the vessel or organ.

Alternatively the flange may be deformable across one or more hinge lines in the flange, allowing parts of the flange to bend back against the tube for insertion into an open in the wall of the vessel or organ.

In one form of the invention the implant is adapted to connect two vessels or hollow organs and is provided with a flange and locking ring at both ends of the tube.

Preferably the tube and the flange are made of a plastics mesh which allows for incorporation of human tissue.

In a further aspect the invention provides a method of connecting two vessels or hollow organs by way of a surgical implant, comprising the steps of: providing a tubular surgical implant adapted to be joined to a wall of a vessel or organ such that the implant opens into the interior of the vessel or organ, said implant comprising an open ended tube, a deformable flange at one end of the tube, a plurality of spikes extending from the flange, alongside and generally parallel to the tube, and a locking ring arranged to slide axially on the tube, the locking ring incorporating a plurality of holes aligned with and adapted to receive the spikes; cutting a hole or slit in the tissue wall of the first vessel or organ, inserting the end of the tube into the hole or slit with the flange deformed, allowing or causing the flange to open behind the tissue wall, engaging the spikes through the tissue wall and sliding the locking ring on the tube until the spikes are engaged with the holes in the locking ring.

BRIEF DESCRIPTION OF DRAWINGS

Notwithstanding any other forms that may fall within its scope, one preferred form of the invention will now be described by way of example only with reference to the accompanying drawings, in which.

MODES FOR CARRYING OUT THE INVENTION

In the preferred form of the invention a tubular surgical implant is provided for use as a by-pass between the aorta and a coronary artery although it will be appreciated that the device may be used in many other applications wherever it is necessary to join an artificial tube with a vessel or organ or to provide a by-pass between different vessels and/or organs. The implant is described as a double-ended device although it will be appreciated that in some applications the engagement flange and locking ring may be provided on one end of the tube only.

The implant comprises a tube (1) having a flange (2) at either end of the tube. The tube and flange may be formed from any suitable materials but are typically of a plastics mesh material such as a grade of GORTEX, an expanded polytetrafluoroethylene (Registered Trade Mark W.L. Gore & Associates, Inc., Newark, Del.) material which allows incorporation of human tissue and a long life for the device in the body.

Each flange is provided with a plurality of spikes (3) extending from the flange, alongside and generally parallel to the tube (1). In this sense the spikes face away from the open end of the tube.

Figure 5:
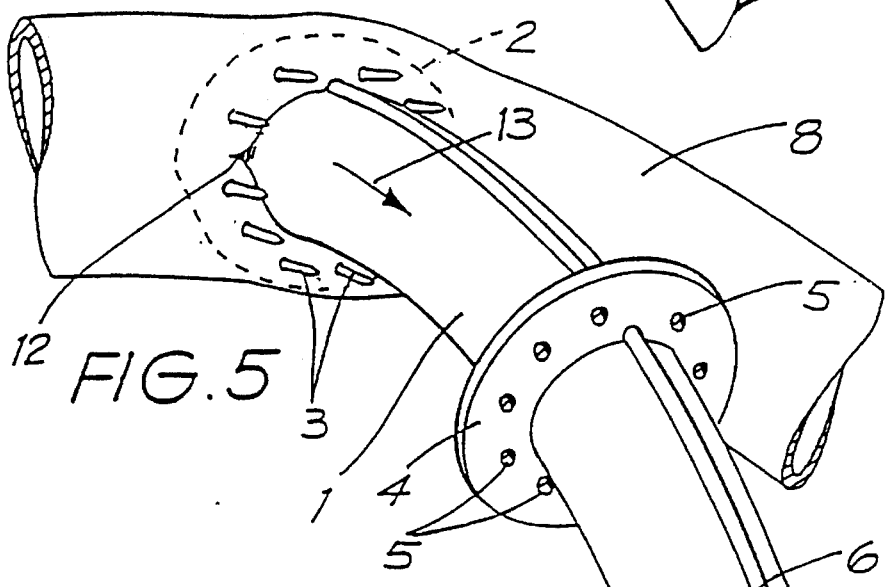
FIG. 5 is a similar view to FIG. 4 showing the spikes of the implant being engaged.

The implant is further provided with locking rings (4) as the same general size and configuration of the flanges (2), the locking rings being arranged to slide axially on the tube (1). Each locking ring incorporates a plurality of holes (5) (FIG. 5) aligned with and adapted to receive the spikes (3) protruding from the corresponding flange (2).

In order to ensure alignment of the holes (5) with the spikes (3) the locking ring may be keyed to the tube by way of a keyway (6) on the tube and a corresponding projection or aperture (not shown) in the locking ring (4), preventing rotation of the ring relative to the tube. In this manner, the holes (5) can be accurately aligned with the spikes (3) enabling the ring to be engaged with the spikes as will be described further below.

Figure 1:
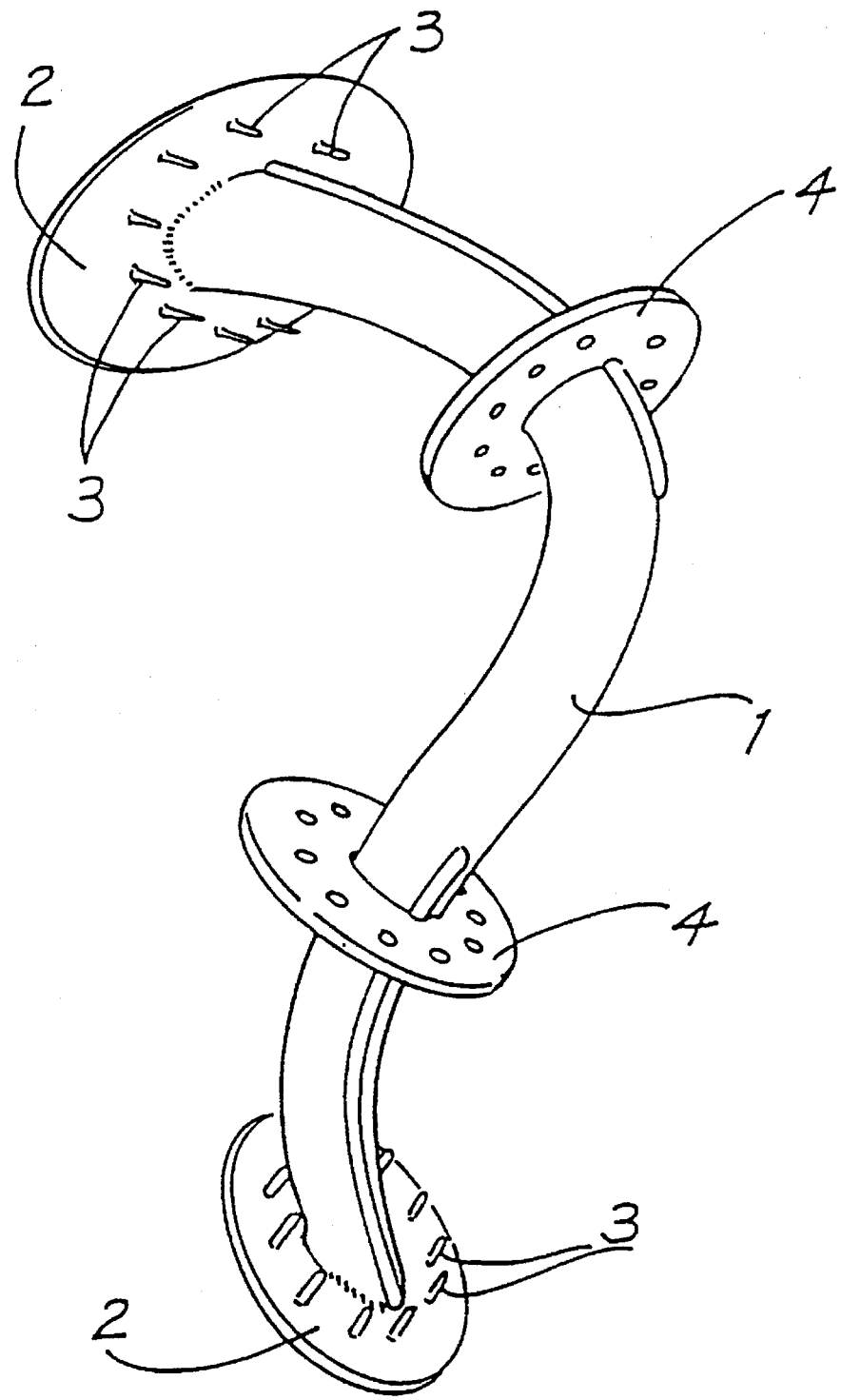
FIG. 1 is a diagrammatic perspective view of a tubular surgical implant according to the invention.
Figure 2:
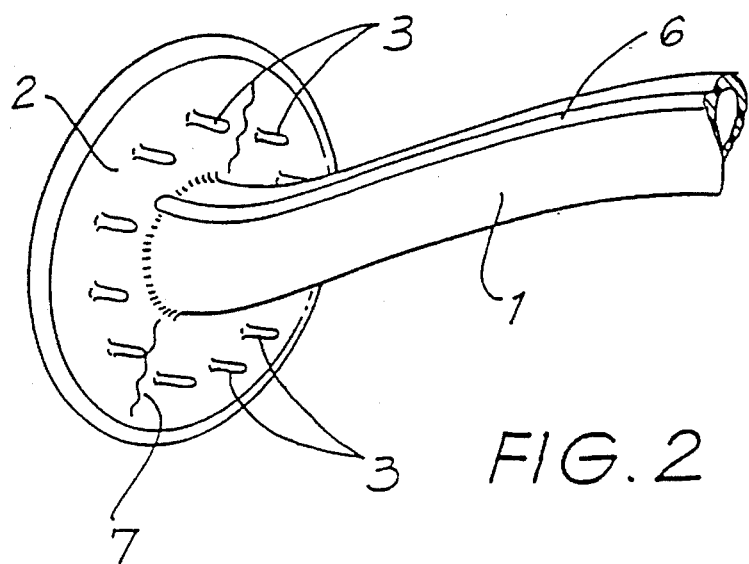
FIG. 2 is a detailed view of one end of the implant shown in FIG. 1.
Figure 4:
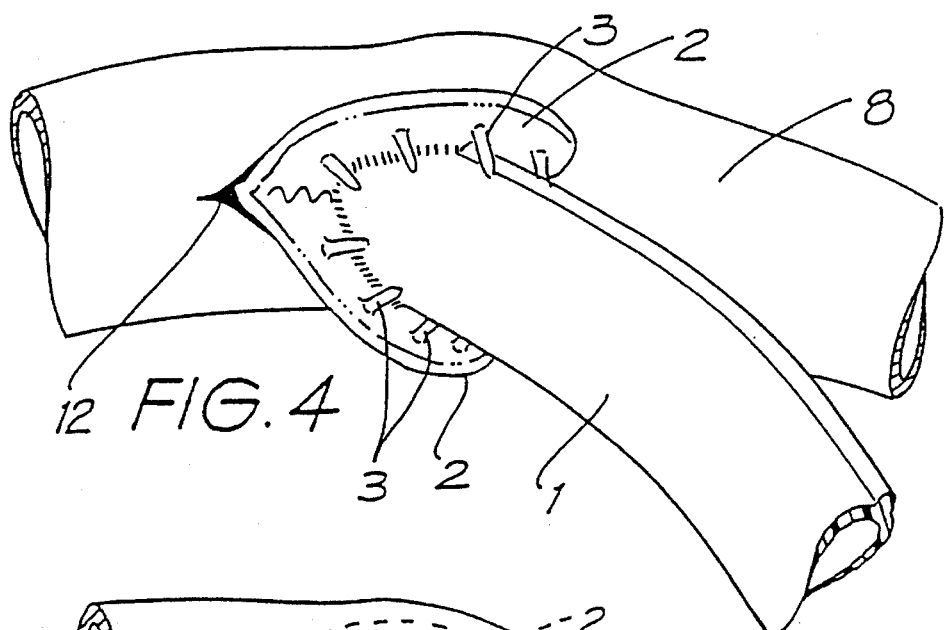
FIG. 4 is a diagrammatic perspective view of the implant being inserted into the incision in the vessel.

The flange (2) is deformable relative to the tube (1) either by deforming the entire flange relative to the tube so that the flange may lie against the tube for insertion into an opening of a vessel or organ, or alternatively the flange maybe deformable across one or more hinge lines (7) (FIG. 2) allowing parts of the flange to bend back against the tube as shown in FIG. 4 for insertion into an opening in the wall of the vessel or organ.

The use of the implant will now be described with reference to a typical coronary by-pass operation where the implant is engaged between the aorta and the distal coronary artery.

Figure 3:
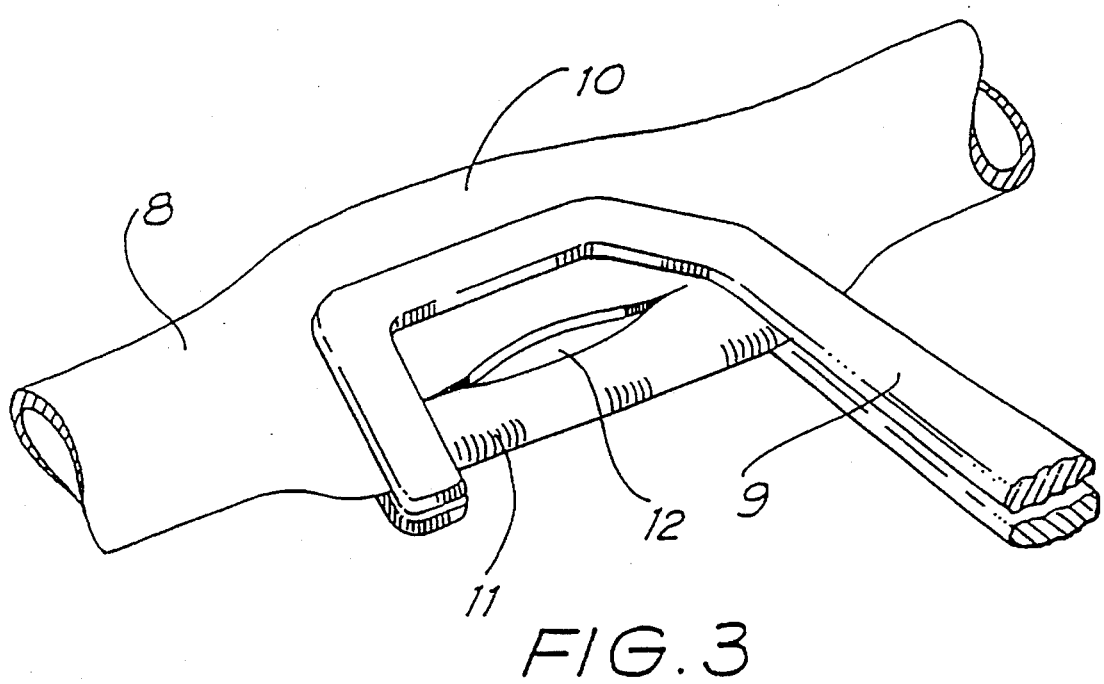
FIG. 3 is a diagrammatic view of a blood vessel clamped and cut preparatory to engagement with the tubular surgical implant shown in FIG. 1.

Referring to FIG. 3 the aorta (8) is first partially clamped by way of a non-traumatic clamp (9) positioned partially across the aorta to allow the continuing flow of blood through unclamped portion (10). The clamped portion (11) of the aorta (8) may then be cut to form an incision (12) for engagement with the implant.

As shown in FIG. 4, the flange (2) may be deformed as previously described and inserted through the incision (12) until the entire flange is positioned within the aorta. The flange is then allowed or caused to open behind the tissue wall of the aorta to its original configuration and the tube pulled back in the direction of arrow (13) (FIG. 5) engaging the spikes (3) through the tissue wall (11).

Figure 6:
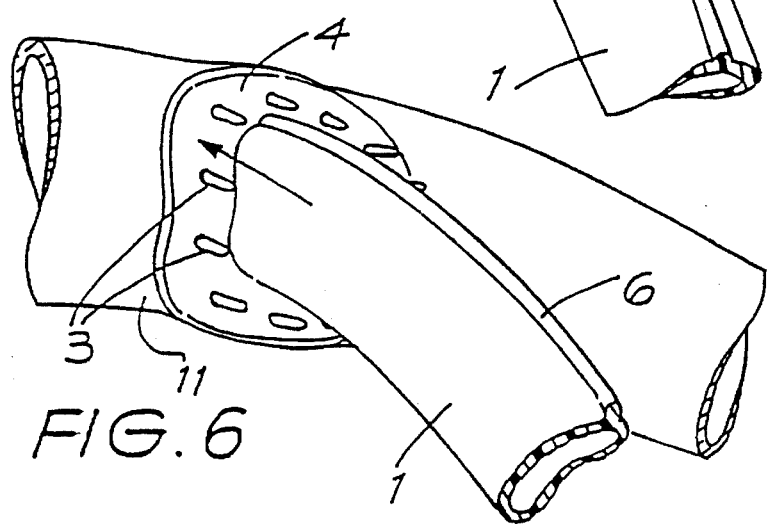
FIG. 6 is a similar view to FIGS. 4 and 5 showing engagement of the locking ring.

The locking ring (4) is then slid down the tube until the spikes (3) are engaged with the holes (5) in the locking ring as shown in FIG. 6.

The spikes (3) and the holes (5) in the locking ring (4) are provided with a series of locking mechanisms arranged to retain the spikes within the holes when the locking ring is engaged with the spikes as shown in FIG. 6. This locking mechanism may take any suitable configuration but is typically a series of "click into place" type of mechanisms which engages the locking ring at various spacings from the flange to allow for several aortic wall thicknesses.

The procedure may then be repeated at the other end of the implant to engage the other flange with the coronary artery, effectively and quickly providing a by-pass between the aorta and the coronary artery.

In the particular application of a heart by-pass operation the flange adapted to be engaged with the coronary artery may be smaller than the flange to be engaged with the aorta to suit the size of the vessel with which it is engaged. A range of different sized and ended device would be used to cover the range expected in different sized diameters and thicknesses of aortas and coronary arteries. In situations where there is more than one blockage in the coronary artery, the tubular surgical implant can be constructed as a manifold with one larger aortic proximal end and several separate coronary distal ends. The tubes may be either parallel sided or tapered (conical) as required for the desized flow rates.

In this manner a surgical implant is provided which enables a coronary by-pass operation to be performed without stopping the heart function or the aorta blood flow to the body and which furthermore does not entail the stripping of veins or arteries from other parts of the body to use as a by-pass conduit.

The implant has application in many other areas presently the province of vascular and microsurgery and may be used wherever it is necessary to join a tube to a vessel or hollow organ or to form a connection between two vessels and/or organs.

I claim:

1. A tubular surgical implant adapted to be joined to a wall of a vessel or hollow organ such that the implant opens into the interior of the vessel or organ, said implant comprising:
   an open-ended tube having a distal end and a proximal end,
   a deformable flange formed at the distal end of the tube for insertion through an opening in the wall of the vessel or hollow organ,
   a plurality of spikes extending from the flange toward the proximal end of the tube, alongside and generally parallel to the tube, and
   a locking ring arranged to slide axially on the tube in a direction from the proximal end of the tube toward the distal end of the tube, the locking ring incorporating a plurality of holes aligned with and adapted to receive the spikes.

2. A tubular surgical implant as claimed in claim 1 wherein the locking ring is keyed to the tube, preventing rotation of the ring relative to the tube.

3. A tubular surgical implant as claimed in claim 1 wherein the spikes and the holes in the locking ring are provided with a locking mechanism arranged to retain the spikes within the holes when the locking ring is engaged with the spikes.

4. A tubular surgical implant as claimed in claim 1 wherein the flange is deformable relative to the tube such that the flange may be deformed to lie against the tube for insertion into an opening in the wall of the vessel or organ.

5. A tubular surgical implant as claimed in claim 1 wherein the flange is deformable across one or more hinge lined in the flange, allowing parts of the flange to bend back against the tube for insertion into an opening in the wall of the vessel or organ.

6. A tubular surgical implant as claimed in claim 1 wherein the implant is adapted to connect two vessels or hollow organs and is provided with a flange and locking ring at both ends of the tube.

7. A tubular surgical implant as claimed in claim 1 wherein the tube and the flange are made of a plastics mesh which allows for incorporation of human tissue.

8. A method of connecting first and second vessels, or first and second hollow organs, or a first vessel and a second hollow organ, by way of a surgical implant, the method comprising the steps of:
   providing a tubular surgical implant adapted to be joined to a tissue wall of a vessel or organ such that the implant opens into the interior of the vessel or organ, the implant comprising an open-ended tube, a deformable flange at one end of the tube, a plurality of spikes extending from the flange, alongside and generally parallel to the tube, and a locking ring arranged to slide axially on the tube, and the locking ring incorporating a plurality of holes aligned with and adapted to receive the spikes;
   cutting an opening in the tissue wall of the first vessel or first organ;
   inserting the end of the tube into the opening with the flange deformed;
   allowing or causing the flange to open behind the tissue wall;
   engaging the spikes through the tissue wall; and
   sliding the locking ring on the tube until the spikes are engaged with the holes in the locking ring.

9. A method as claimed in claim 8 wherein the area of the first vessel or the first organ surrounding the opening is isolated from the remainder of the first vessel or the first organ by way of a clamp before making the opening, in a manner allowing fluid to continue to flow through the remainder of the vessel or organ.

10. A method as claimed in claim 8 wherein the first vessel or the first organ comprises an aorta and the second vessel or the second organ comprises a distal coronary artery.

* * * * *